US012714486B2

(12) United States Patent
Shen et al.

(10) Patent No.: US 12,714,486 B2
(45) Date of Patent: Aug. 25, 2026

(54) CRYOBALLOON CONTROL APPARATUS, CATHETER SYSTEM, AND TEMPERATURE DISPLAY METHOD

(71) Applicant: SHANGHAI MICROPORT EP MEDTECH CO., LTD., Shanghai (CN)

(72) Inventors: Liuping Shen, Shanghai (CN); Degui Pang, Shanghai (CN); Yiyong Sun, Shanghai (CN); Jinfeng Liu, Shanghai (CN); Qingchun Zhang, Shanghai (CN)

(73) Assignee: SHANGHAI MICROPORT EP MEDTECH CO., LTD., Shanghai (CN)

( * ) Notice: Subject to any disclaimer, the term of this patent is extended or adjusted under 35 U.S.C. 154(b) by 1028 days.

(21) Appl. No.: 17/909,235

(22) PCT Filed: Feb. 18, 2021

(86) PCT No.: PCT/CN2021/076770

§ 371 (c)(1),
(2) Date: Sep. 2, 2022

(87) PCT Pub. No.: WO2021/175117

PCT Pub. Date: Sep. 10, 2021

(65) Prior Publication Data

US 2023/0097773 A1 Mar. 30, 2023

(30) Foreign Application Priority Data

Mar. 4, 2020 (CN) ......................... 202010144050.2

(51) Int. Cl.
*A61B 18/02* (2006.01)
*A61B 18/00* (2006.01)

(52) U.S. Cl.
CPC .... *A61B 18/02* (2013.01); *A61B 2018/00714* (2013.01); *A61B 2018/00744* (2013.01); *A61B 2018/0212* (2013.01)

(58) Field of Classification Search
CPC .......... A61B 18/02; A61B 2018/00714; A61B 2018/00744; A61B 2018/0212;
(Continued)

(56) References Cited

U.S. PATENT DOCUMENTS 5,501,681 A 3/1996 Neuwrith et al.
2008/0312644 A1* 12/2008 Fourkas ................. A61B 18/02 606/22

(Continued)

FOREIGN PATENT DOCUMENTS

CN 105682589 A 6/2016
CN 106963344 A 7/2017

(Continued)

*Primary Examiner* — Niketa Patel
*Assistant Examiner* — Joshua Brendon Solomon
(74) *Attorney, Agent, or Firm* — MUNCY, GEISSLER, OLDS & LOWE, P.C.

(57) ABSTRACT

A cryoballoon control device (2), catheter system and temperature display method are disclosed. The control device (2) acquires a plurality of balloon circumference temperature values obtained by circumference temperature sensors (4) circumferentially disposed on a cryoballoon (1) and a balloon center temperature value obtained from a center temperature sensor (5) disposed at a center of the cryoballoon (1) and, automatically adjusts a flow rate of a coolant introduced into the cryoballoon (1) based on a comparison between a preset balloon temperature value and a comparative temperature value, to enable a temperature adjustment to the cryoballoon (1), wherein the comparative temperature value is the balloon center temperature value, any one of the balloon circumference temperature values, or a computational temperature value derived by a predefined algorithm (Continued)

from the plurality of balloon circumference temperature values. The cryoballoon catheter system is configured to display, on the display device (3), a plurality of balloon circumference temperature representation graphs surrounding a balloon center temperature representation graph, wherein when one of the balloon circumference temperature values exceeds a first predetermined threshold range, a corresponding one of the balloon circumference temperature representation graphs indicates a first alert condition which prompts an operator to adjust temperature of the cryoballoon (1).

17 Claims, 4 Drawing Sheets

(58) Field of Classification Search
CPC .. A61B 2018/0022; A61B 2018/00577; A61B 2018/00642; A61B 2018/00666; A61B 2018/00797; A61B 2018/0262; A61B 2018/00023; A61B 2018/00791; A61B 2018/00898
See application file for complete search history.

(56) References Cited

U.S. PATENT DOCUMENTS

2009/0299356 A1* 12/2009 Watson ............ A61M 25/1006 606/21
2010/0069836 A1 3/2010 Satake
2011/0092967 A1* 4/2011 Harvey-Poncelet ........................ A61M 25/0113 604/246
2012/0265188 A1 10/2012 Buchbinder et al.
2014/0066913 A1* 3/2014 Sherman ............ A61B 18/1492 606/41
2015/0018809 A1* 1/2015 Mihalik ................ A61B 18/02 606/21
2016/0157913 A1 6/2016 Coulombe et al.
2017/0105627 A1 4/2017 Katz et al.
2018/0310989 A1* 11/2018 Mcguckin, Jr. ...... A61B 5/4836
2018/0338787 A1* 11/2018 Cote ..................... A61B 90/98
2019/0082969 A1 3/2019 Flaherty et al.

FOREIGN PATENT DOCUMENTS

CN 107019497 A 8/2017
CN 109498145 A 3/2019
CN 109549703 A 4/2019
CN 109589169 A 4/2019
CN 109646106 A 4/2019
CN 109738027 A 5/2019
CN 209332253 U 9/2019
CN 110573100 A 12/2019
CN 111329575 A 6/2020
EP 1735041 A4 4/2008
EP 1980287 A2 10/2008

* cited by examiner

CRYOBALLOON CONTROL APPARATUS, CATHETER SYSTEM, AND TEMPERATURE DISPLAY METHOD

TECHNICAL FIELD

The present invention relates to the field of medical equipments and, in particular, to a cryoballoon control device, catheter system and temperature display method.

BACKGROUND

At present, cryoablation has been widely used in the treatment of tachyarrhythmia such as atrial fibrillation (AF). Arrhythmia treatment by cryoablation is achieved by destroying a target site identified as a source of aberrant electrophysiological activity associated with arrhythmia by applying thereto a cryogenic liquid, which absorbs heat by evaporation and takes away the heat from tissue and thereby lowers its temperature and "freezes and kills" cells at the target site. A lot of clinical data has shown that, compared to other ablation techniques, cryoablation allows easier physician learning and operation, a shorter procedure time, improved treatment effectiveness, reduced risk of the occurrence of thrombosis and other serious complications, and less patient pain.

Currently used cryoablation systems include a cryoablation system and a cryoballoon catheter. Temperature control and display in a cryoablation procedure are main factors that affect ablation effectiveness. It is generally believed that an effective "cold burn" of tissue that can provide an effect of pulmonary vein isolation can be achieved at −60° C. Existing cryoballoon catheters are equipped with only one temperature monitoring point which is disposed inside the balloon, despite the fact that what an operator desires to know is the actual temperature of the location where the balloon is brought into contact with tissue. Therefore, the existing designs cannot provide an operator with intuition and have to rely on the operator's experience. In addition, typical cryoablation apparatuses do not have the function to control a target temperature. Once ablation begins, the ablation temperature will rapidly drop in an uncontrolled manner possibly to an excessively low level which may cause serious complications. Therefore, it is desirable to have a cryoablation system, which is not only able to control the target temperature but also has an intuitive interface that provides an operator with intuition about tissue temperature variation across several locations. Thus, it can provide the operator with more valuable surgical information and hence enables increased surgical safety.

SUMMARY OF THE INVENTION

It is an object of the present invention to provide a cryoballoon control device, catheter system and temperature display method, which solve the problem that conventional cryoablation apparatuses are not able to display temperature intuitively and to control temperature conveniently.

To this end, in a first aspect of the present invention, there is provided a cryoballoon control device connected to a cryoballoon catheter. The control device is configured to: acquire a plurality of balloon circumference temperature values obtained by a plurality of circumference temperature sensors, and a balloon center temperature value obtained by a center temperature sensor; and automatically adjust a flow rate of a coolant introduced into a cryoballoon in the cryoballoon catheter based on a comparison between a preset balloon temperature value and a comparative temperature value to enable a temperature control of the cryoballoon, wherein the comparative temperature value is the balloon center temperature value, or any one of the plurality of balloon circumference temperature values, or a computational temperature value derived by a predefined algorithm from the plurality of balloon circumference temperature values.

Optionally, when the comparative temperature value is a computational temperature value derived by a predefined algorithm from the plurality of balloon circumference temperature values, the predefined algorithm may comprise any one of:

determining a lowest one of the plurality of balloon circumference temperature values as the computational temperature value;

determining an average of the plurality of balloon circumference temperature values as the computational temperature value;

determining an average of the balloon circumference temperature values that are lower than the balloon center temperature value as the computational temperature value; and determining a lowest one of the balloon circumference temperature values that are lower than the balloon center temperature value as the computational temperature value.

In a second aspect of the present invention, there is provided cryoballoon catheter system comprising the control device as defined above, a cryoballoon catheter and a display device. The cryoballoon catheter comprises a cryoballoon, a center temperature sensor disposed at a center of the cryoballoon and a plurality of circumference temperature sensors circumferentially disposed on the cryoballoon. The center temperature sensor and the circumference temperature sensors are both communicatively connected to the control device. The display device is communicatively connected to the control device. The display device is provided with an input field for receiving a preset balloon temperature. The cryoballoon catheter system configured to:

display a balloon center temperature representation graph on the display device based on the balloon center temperature value; and display a plurality of balloon circumference temperature representation graphs on the display device based on the plurality of balloon circumference temperature values, wherein the plurality of balloon circumference temperature representation graphs surround the balloon center temperature representation graph, wherein in an event of any one of the plurality of balloon circumference temperature values exceeding a first predetermined threshold range, a corresponding one of the balloon circumference temperature representation graphs indicates a first alert condition to prompt an operator to adjust a temperature of the cryoballoon.

Optionally, the balloon circumference temperature representation graph may comprise balloon circumference temperature condition graph configured to indicate a normal condition or the first alert condition, wherein the normal condition indicates that the balloon circumference temperature value obtained by a corresponding circumference temperature sensor lies within the first threshold range, to tell the operator that a temperature of the cryoballoon is appropriate.

Optionally, a plurality of the balloon circumference temperature condition graphs may be annularly arranged to form an annulus, wherein a circumferential location of each of the balloon circumference temperature condition graphs in the annulus is in correspondence with a circumferential location of a corresponding circumference temperature sensor on the cryoballoon.

Optionally, the first alert condition may comprise a lower limit exceeded alert condition and an upper limit exceeded alert condition, wherein the lower limit exceeded alert condition indicates that the balloon circumference temperature value obtained by the corresponding circumference temperature sensor is lower than a lower limit of the first threshold range, and wherein the upper limit exceeded alert condition indicates that the balloon circumference temperature value obtained by the corresponding circumference temperature sensor is higher than an upper limit of the first threshold range.

Optionally, the balloon circumference temperature representation graph may comprise a balloon circumference temperature curve plot, wherein the balloon circumference temperature curve plot may comprise curves of the balloon circumference temperature values obtained by the corresponding circumference temperature sensors varying over time.

Optionally, the balloon circumference temperature curve plot may comprise an indication of the first alert condition, wherein the first alert condition comprises a flashing or bold display of the balloon circumference temperature curve plot, and/or wherein the balloon circumference temperature representation graph further comprises a lower limit temperature line of the first threshold range.

Optionally, the balloon circumference temperature representation graph may comprise a balloon graph, wherein the balloon graph comprises a plurality of dots corresponding to the plurality of circumference temperature sensors and/or the center temperature sensor, wherein a location of each dot in the balloon graph is in correspondence with a location of a corresponding one of the circumference temperature sensors and/or the center temperature sensor on the cryoballoon.

Optionally, the cryoballoon catheter system may be further configured to: display historical ablation data of a plurality of ablation zones on the display device and provide press buttons for the operator to select one of current ablation zones.

Optionally, the cryoballoon catheter system may be further configured to display inflation condition of the cryoballoon on the display device, wherein the inflation condition of the cryoballoon comprises at least one of: an internal pressure of the cryoballoon, the balloon center temperature value, an inflation time, an inflation flow rate and an inflation pressure.

Optionally, in an event of the internal pressure of the cryoballoon exceeding a second predetermined threshold range, or of the balloon center temperature value exceeding a third predetermined threshold range, the inflation condition of the cryoballoon may be displayed in a manner indicating a second alert condition.

Optionally, the cryoballoon catheter system may be further configured to:

provide, on the display device, an input field for receiving an ablation time and press buttons, “Start”, “Pause” and “Emergency Stop”, wherein when the press button “Start” is pressed, the cryoballoon catheter performs a cryoablation operation according to the received preset balloon temperature and an ablation time, and the system automatically adjusts a flow rate to the coolant based on a comparison between the comparative temperature value and the preset balloon temperature value, wherein when the press button “Pause” is pressed, the system pauses the cryoablation operation, and wherein when the press button “Emergency Stop” is pressed, the system stops performing the cryoablation operation.

Optionally, when the press button “Start” is pressed, the display device may be further configured to display at least one of: a curve of the computational temperature value varying over time, an internal pressure of the cryoballoon and the ablation time.

Optionally, the cryoballoon catheter system may be further configured to:

after a cryogenic gas supply to the cryoballoon catheter is cut off, display, on the display device, the plurality of balloon circumference temperature representation graphs, the balloon center temperature representation graph, a rewarming time and the internal pressure of the cryoballoon.

In a third aspect of the present invention, there is provided a temperature display method using the cryoballoon catheter system as defined above, which comprises:

acquiring a plurality of balloon circumference temperature values obtained by a plurality of circumference temperature sensors disposed on a cryoballoon and a balloon center temperature value obtained by a center temperature sensor disposed at a center of the cryoballoon;

displaying a plurality of balloon circumference temperature representation graphs based on the plurality of balloon circumference temperature values, and displaying a balloon center temperature representation graph based on the balloon center temperature value, wherein the plurality of balloon circumference temperature representation graphs surround the balloon center temperature representation graph; and in an event of any one of the plurality of balloon circumference temperature values exceeding a first predetermined threshold range, displaying a corresponding one of the balloon circumference temperature representation graphs in a manner indicating a first alert condition to prompt an operator to adjust a temperature of the cryoballoon catheter.

Optionally, the balloon circumference temperature representation graph may comprise balloon circumference temperature condition graphs, wherein a plurality of the balloon circumference temperature condition graphs are annularly arranged to form an annulus in such a manner, and wherein a circumferential location of each of the balloon circumference temperature condition graphs in the annulus is in correspondence with a circumferential location of a corresponding circumference temperature sensor on the cryoballoon.

In summary, in the cryoballoon control device, catheter system and temperature display method of the present invention, based on balloon circumference temperature values obtained by a plurality of circumference temperature sensors circumferentially disposed on a cryoballoon catheter, a plurality of balloon circumference temperature representation graphs are displayed on a display device. Moreover, based on a balloon center temperature value obtained by a center temperature sensor disposed at a center of the cryoballoon catheter, a balloon center temperature representation graph is displayed on the display device. The balloon circumference temperature representation graphs are displayed in such an intuitive manner that they surround the balloon center temperature representation graph. In the event of any one of the balloon circumference temperature values exceeding a first predetermined threshold range, a corresponding one of the balloon circumference temperature representation graphs is displayed in a manner indicating a first alert condition, promoting an operator to adjust temperature of the cryoballoon. A preset balloon temperature is received in an input field displayed on the display device, and based on a comparison between the preset balloon temperature value and a comparative temperature value, a flow rate adjustment is automatically made to a coolant introduced into the cryoballoon, thus achieving temperature control of the cryoballoon. The comparative temperature value is: the balloon center temperature value, any one of the balloon circumference temperature values, or a computational temperature value derived by a predefined algorithm from the plurality of balloon circumference temperature values. With this arrangement, on the one hand, it is allowed to determine whether the temperatures of the individual cryoballoon portions stay within the appropriate temperature range in an intuitive manner. Moreover, in the event of the temperature of any cryoballoon portion exceeding the first predetermined threshold range, the corresponding balloon circumference temperature representation graph is displayed in a manner indicating the first alert condition, thereby guiding the operator to adjust temperature of the cryoballoon. On the other hand, the input field provided on the display device can receive the preset balloon temperature from the operator, and the system then compares the preset balloon temperature value with the comparative temperature value. Based on the comparison, a flow rate adjustment is automatically made to the coolant, thereby achieving temperature control of the cryoballoon in a simple and reliable manner. In particular, since the comparative temperature value is the balloon center temperature value, any one of the balloon circumference temperature values, or a computational temperature value derived by the predefined algorithm from the plurality of balloon circumference temperature values, the system is widely applicable and highly accurate.

BRIEF DESCRIPTION OF THE DRAWINGS

Those of ordinary skill in the art would appreciate that the following drawings are presented merely to enable a better understanding of the present invention rather than to limit the scope thereof in any sense. In the drawings.

DESCRIPTION OF REFERENCE NUMERALS IN DRAWINGS

1: Cryoablation; 2: Control Device; 3: Display Device; 4: Circumference Temperature Sensor; 5: Center Temperature Sensor;

11: Balloon Circumference Temperature Condition Graph; 111: Normal Condition; 112: First Alert Condition; 12: Balloon Circumference Temperature Curve Plot; 120: Balloon Center Temperature Curve; 121: Balloon Circumference Temperature Curve; 13: Lower Limit Temperature Line; 14: Balloon graph; 140: Dot; 15: Balloon Inflation Representation Graph;

M1: Ready Interface; M2: Inflation Interface; M3: Ablation Interface; M4: Rewarming Interface.

DETAILED DESCRIPTION

Objects, features and advantages of the present invention will become more apparent upon reading the following more detailed description of the present invention, which is set forth by way of particular embodiments with reference to the accompanying drawings. Note that the figures are provided in a very simplified form not necessarily drawn to exact scale and for the only purpose of facilitating easy and clear description of the embodiments. In addition, the structures shown in the figures are usually partially representations of their actual counterparts. In particular, as the figures would have different emphases, they are sometimes drawn to different scales.

As used herein, the singular forms "a", "an" and "the" include plural referents, and the phrase "plurality of" means two or more, unless the context clearly dictates otherwise. As used herein, the term "or" is generally employed in the sense of "and/or", unless the context clearly dictates otherwise. The term "proximal" usually refers to an end closer to an operator, while the term "distal" usually refers to an end closer to a diseased site in a patient.

The present invention provides a catheter system for a cryoballoon, which solves the problem that conventional cryoablation apparatuses are incapable of intuitive temperature display and convenient temperature control.

The following description is set forth with reference to the accompanying drawings.

Figure 1:
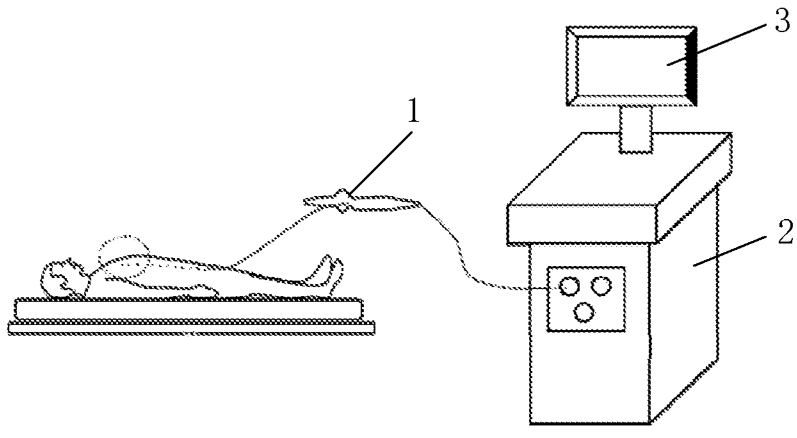
FIG. 1 is a schematic diagram of a catheter system for a cryoballoon according to an embodiment of the present invention.
Figure 2:
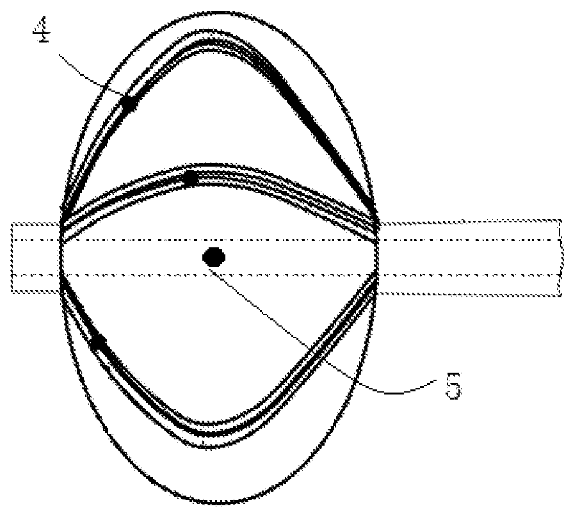
FIG. 2 is a schematic diagram of the cryoballoon of FIG. 1, showing circumference temperature sensors disposed circumferentially on the cryoballoon and a center temperature sensor disposed at a center of the cryoballoon.
Figure 3:
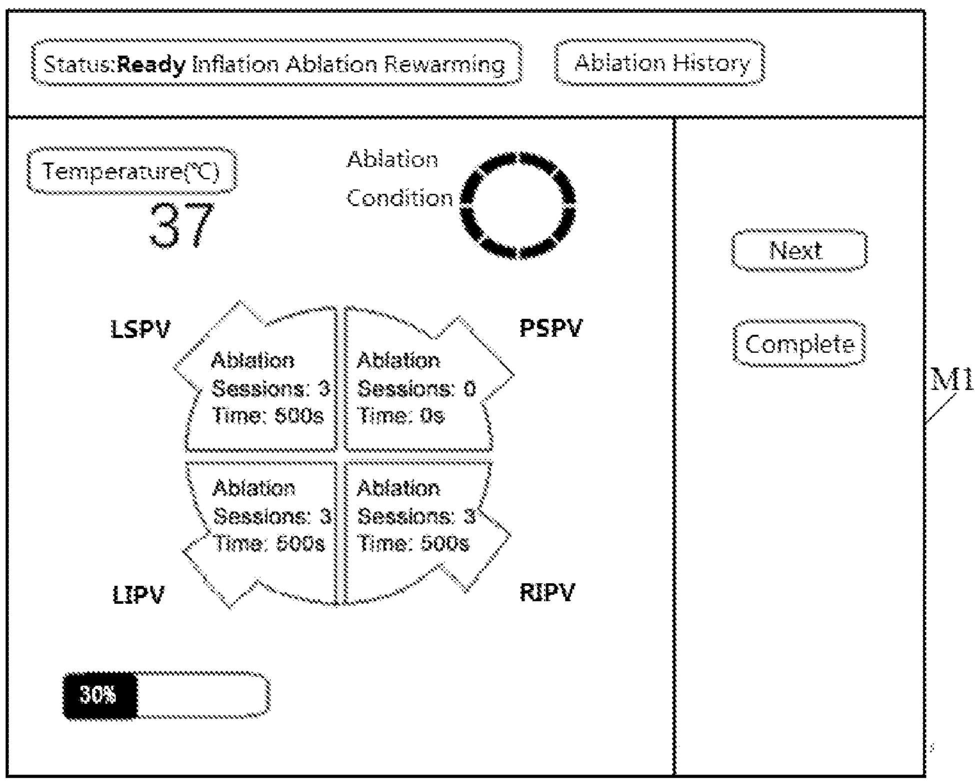
FIG. 3 is a schematic diagram of a ready interface displayed on a display device according to an embodiment of the present invention.
Figure 4:
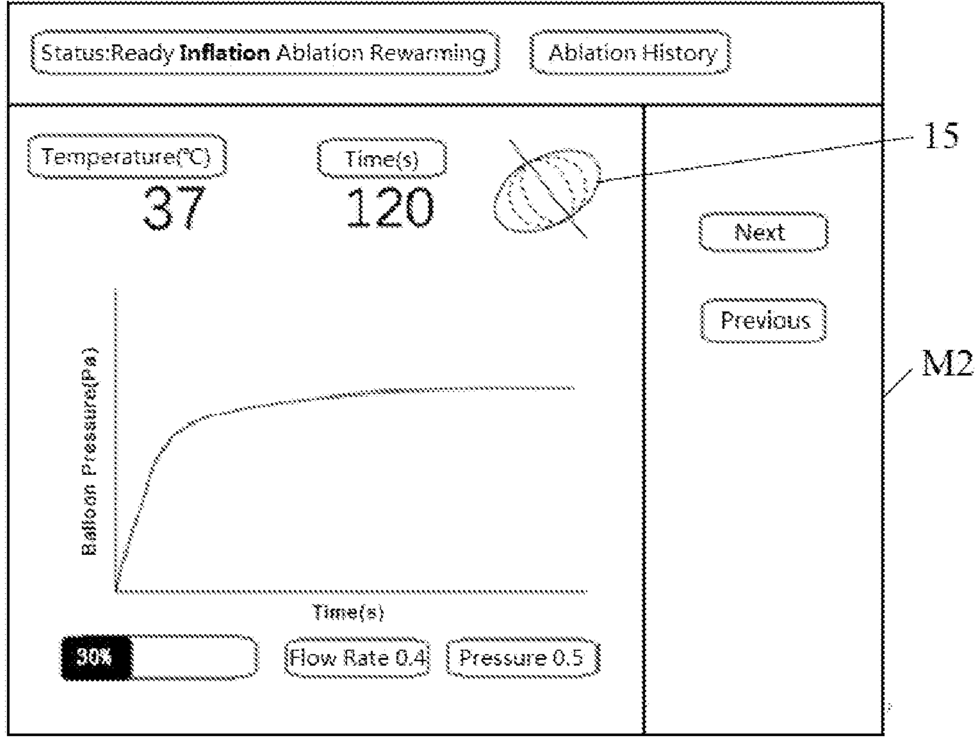
FIG. 4 is a schematic diagram of an inflation interface displayed on the display device according to an embodiment of the present invention.
Figure 5:
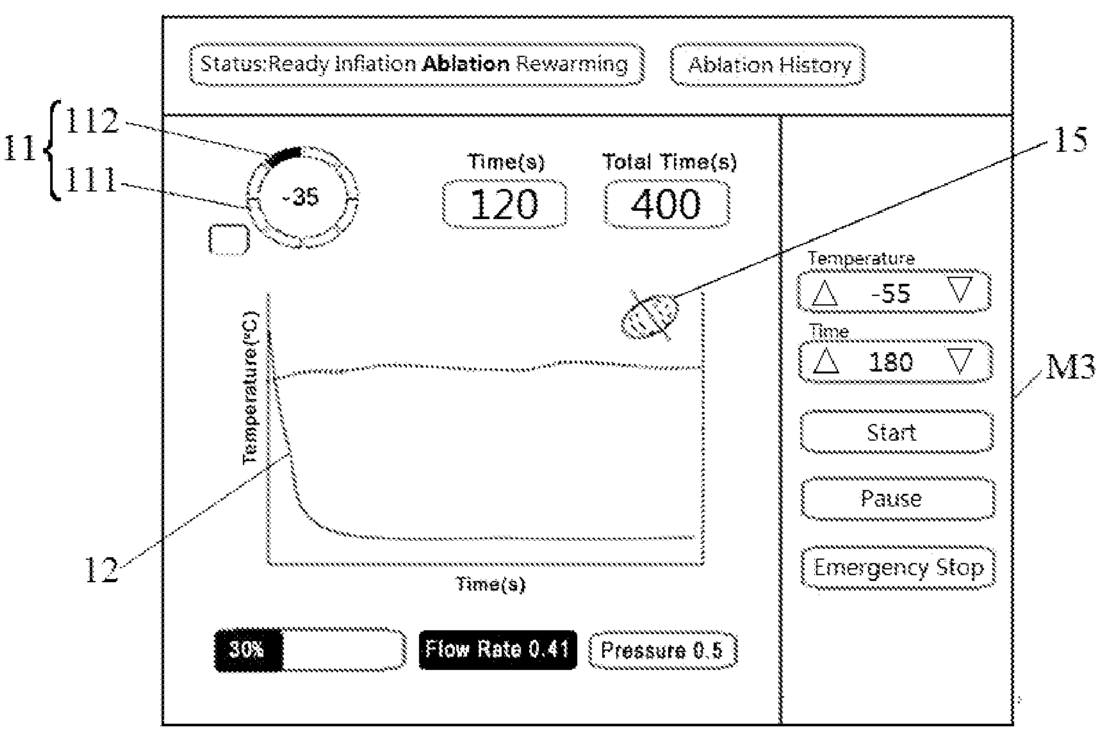
FIG. 5 is a schematic diagram of a first ablation interface displayed on the display device according to an embodiment of the present invention.
Figure 6:
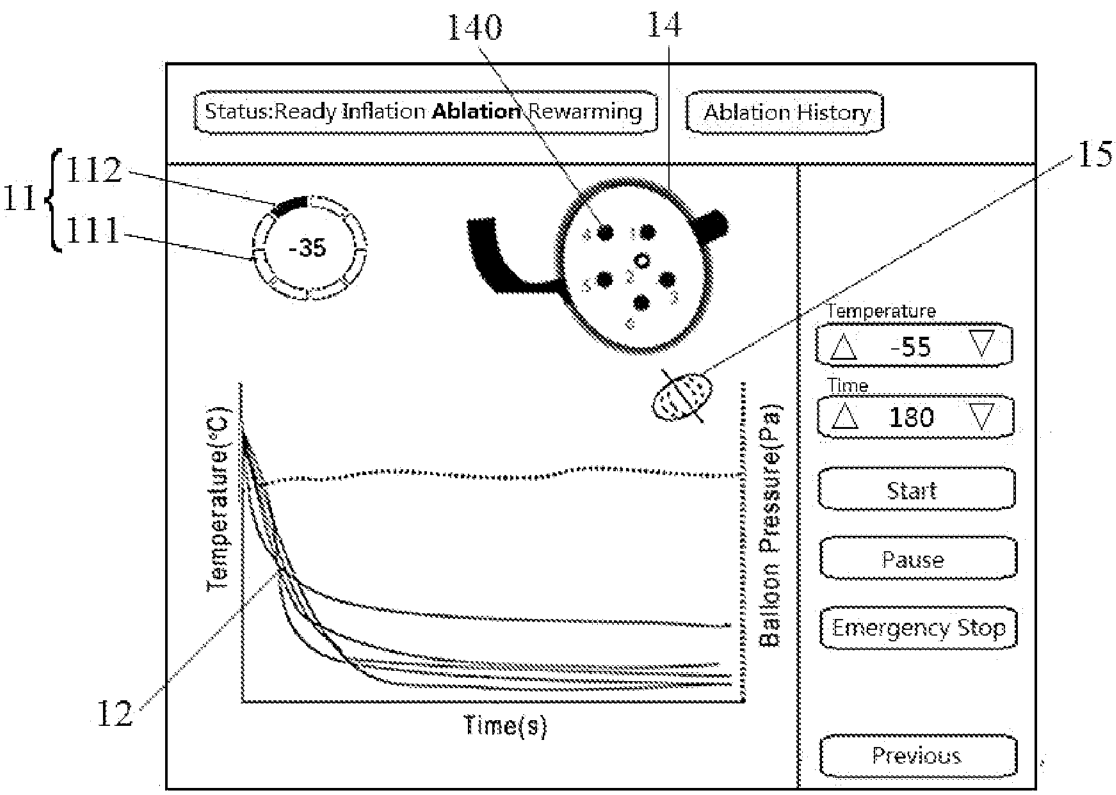
FIG. 6 is a schematic diagram of a second ablation interface displayed on the display device according to an embodiment of the present invention.
Figure 7:
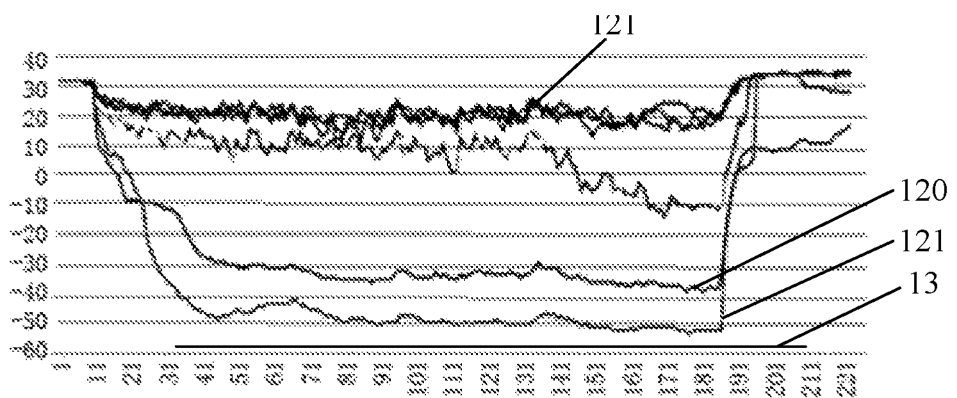
FIG. 7 shows a balloon circumference temperature curve plot according to an embodiment of the present invention.
Figure 8:
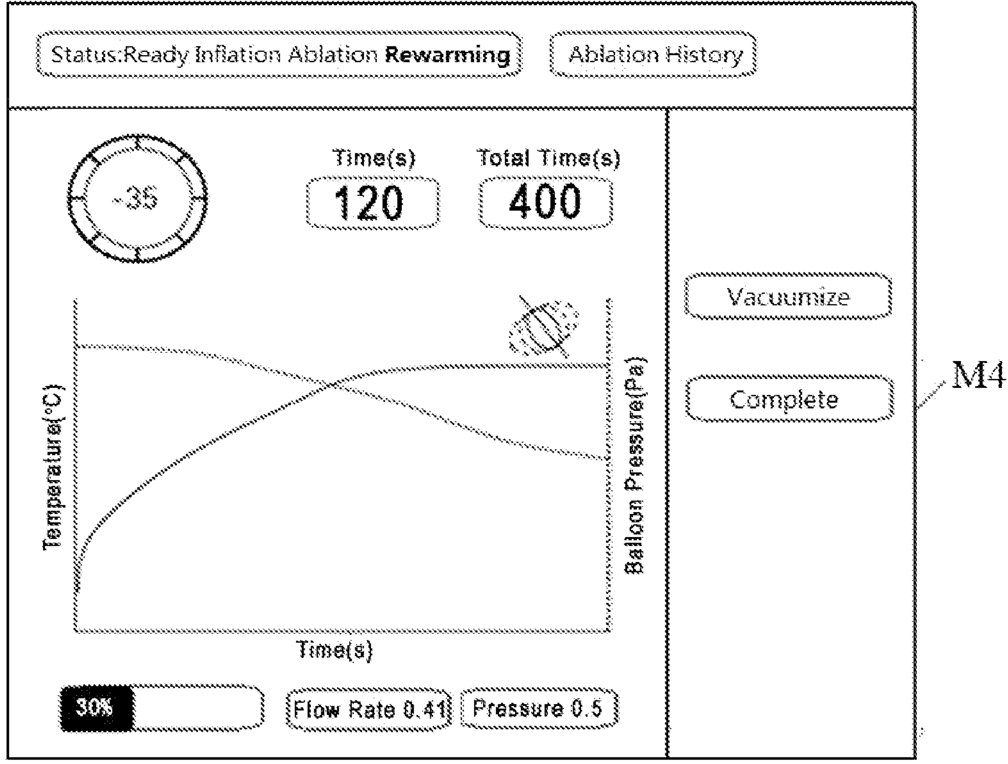
FIG. 8 is a schematic diagram of a rewarming interface displayed on the display device according to an embodiment of the present invention.

Reference will now be made to FIGS. 1 through 8. FIG. 1 is a schematic diagram of a catheter system for a cryoballoon according to an embodiment of the present invention. FIG. 2 is a schematic diagram of the cryoballoon of FIG. 1. FIG. 3 is a schematic diagram of a ready interface displayed on a display device according to an embodiment of the present invention. FIG. 4 is a schematic diagram of an inflation interface displayed on the display device according to an embodiment of the present invention. FIG. 5 is a schematic diagram of a first ablation interface displayed on the display device according to an embodiment of the present invention. FIG. 6 is a schematic diagram of a second ablation interface displayed on the display device according to an embodiment of the present invention. FIG. 7 shows a balloon circumference temperature curve plot according to an embodiment of the present invention. FIG. 8 is a schematic diagram of a rewarming interface displayed on the display device according to an embodiment of the present invention.

As shown in FIG. 1, a catheter system for a cryoballoon according to an embodiment of the present invention includes a cryoballoon catheter, a control device 2 and a display device 3. The cryoballoon catheter includes a cryoballoon 1, and the control device 2 includes a readable storage medium storing a program thereon. The cryoballoon 1 includes a center temperature sensor 5 disposed at a center of the cryoballoon 1 (as shown in FIG. 2) and a plurality of circumference temperature sensors 4 circumferentially disposed on the cryoballoon 1 (as shown in FIG. 2). The center and circumference temperature sensors are all communicatively connected to the control device 2. The display device 3 is also communicatively connected to the control device 2. Optionally, the catheter system for a cryoballoon further includes a cryoablation apparatus connected to the cryoballoon catheter. During use for cryoablation, the cryoballoon 1 is delivered into the left atrium through a vascular access. The cryoablation apparatus is mainly adapted to provide the cryoballoon 1 with cryogenic energy and to detect a temperature of the cryoballoon 1 at the same time. The cryoablation procedure essentially involves: delivering the cryoballoon 1 of the cryoballoon catheter into the left atrium through the vascular access; inflating the cryoballoon 1; placing the cryoballoon 1 at a target ablation site with the aid of X-ray imaging; radiographically determining whether the cryoballoon 1 has achieved desirable occlusion; conducting cryoablation; stopping ablation and rewarming the balloon; withdrawing the cryoballoon 1 and relocating it to the next target ablation site. Those skilled in the art may configure the catheter system in a conventional way, a detailed description of which is omitted herein.

In order to solve the problem that conventional catheter systems are not able to display the temperature intuitively and to control the temperature conveniently, according to the present invention, the control device 2 is improved, as described in detail below by way of a preferred embodiment of the present invention.

When the program stored on the readable storage medium of the control device 2 is executed, the following steps will be carried out.

S1: acquiring a plurality of balloon circumference temperature values from the plurality of circumference temperature sensors, and a balloon center temperature value from the center temperature sensor (i.e., each of the balloon circumference temperature values is acquired from a corresponding one of the circumference temperature sensors).

S2: displaying a plurality of balloon circumference temperature representation graphs on the display device 2 based on the plurality of balloon circumference temperature values, wherein the plurality of balloon circumference temperature representation graphs are displayed around a balloon center temperature representation graph.

S3: displaying the balloon center temperature representation graph on the display device 2 based on the balloon center temperature value. It would be appreciated that steps S2 and S3 is not limited to being performed in any sequential order. They may be performed either simultaneously or successively.

If any one of the plurality of balloon circumference temperature values is beyond a first threshold range, then a corresponding one of the balloon circumference temperature representation graphs will be displayed in a manner indicating a first alert condition, prompting an operator to adjust temperature of the cryoballoon catheter. Moreover, an input field for receiving a preset balloon temperature is displayed on the display device 2, and a comparison is drawn between the preset balloon temperature value and a comparative temperature value. Based on a result of the comparison, a flow rate of a coolant introduced into the cryoballoon 1 is automatically adjusted, thereby achieving temperature control of the cryoballoon. The comparative temperature value may be any one of the balloon center temperature value and the plurality of balloon circumference temperature values, or a computational temperature value derived by a predefined algorithm from the plurality of balloon circumference temperature values.

With this arrangement, it is possible to intuitively display and to check whether the temperatures at individual portions of the cryoballoon 1 (essentially, peripheral circumference portions thereof) are within a suitable temperature range. If the temperature of a certain one of the portions of the cryoballoon 1 is beyond the predetermined first threshold range, a corresponding one of the balloon circumference temperature representation graphs will be displayed in a manner that indicates the first alert condition, guiding the operator to adjust temperature of the cryoballoon catheter. During cryoablation procedure, a good fit and good occlusion of the balloon at the ablation site is crucial to the effectiveness of the entire procedure. Whether the balloon has achieved desirable occlusion can be determined based on temperature cooling rates at different portions of the balloon. During cryoablation, an excessively low temperature applied to local tissue may cause severe complications and directly affect the safety of the procedure. Therefore, the plurality of balloon circumference temperature representation graphs allow the operator to intuitively obtain useful information (e.g., temperature conditions of the balloon circumference portions), thus providing the operator with better surgical guidance. Further, the input field provided on the display device 2 can receive a preset balloon temperature from the operator. The system then compares the preset balloon temperature value with a comparative temperature value and, based on a result of the comparison, automatically adjusts a flow rate of the coolant, thereby achieving temperature control over the cryoballoon 1 in a simple and reliable manner. In particular, the comparative temperature value is any one of the balloon center temperature value and the plurality of balloon circumference temperature values, or a computational temperature value derived by a predefined algorithm from the plurality of balloon circumference temperature values. This makes the system widely applicable and highly accurate.

In practice, the computational temperature value may be configured to be equal to one of the balloon circumference temperature values to conduct a proportional-integral-derivative (PID) control. Alternatively, the computational temperature value may be determined by a predefined algorithm based on some or all of the plurality of balloon circumference temperature values. The predefined algorithm may comprise any one of the algorithms detailed below.

F1: The lowest one of the balloon circumference temperature values is chosen as the computational temperature value. All the balloon circumference temperature values are compared to determine a balloon circumference portion with the lowest balloon circumference temperature value, and temperature control is conducted over the balloon circumference portion with the lowest balloon circumference temperature value to make it not lower than the preset balloon temperature. This algorithm can ensure that the lowest temperature throughout the entire balloon surface is not lower than the preset balloon temperature, thus guaranteeing safety of the cryoablation procedure.

F2: An average of all the balloon circumference temperature values is determined as the computational temperature value. With the temperature of the entire balloon taken as a reference, all the balloon circumference temperature values at the surface of the entire balloon are averaged to derive the computational temperature value. This can avoid measurement fluctuations in a single balloon circumference temperature value from introducing unnecessary fluctuations to flow rate control.

F3: Selecting all balloon circumference temperature values that are lower than the balloon center temperature value, and an average of those in the balloon circumference temperature values that are lower than the balloon center temperature value is determined as the computational temperature value. Based on a comparison between the plurality of balloon circumference temperature values and the balloon center temperature value, a proper temperature control method is chosen. For instance, with the balloon center temperature value taken as the aforementioned comparative value, if only one of the balloon circumference temperature value is lower than the balloon center temperature value, then this balloon circumference temperature value is chosen as the computational temperature value for target temperature control. If a number of the balloon circumference temperatures are lower than the balloon center temperature, then an average of the number of balloon circumference temperature values is taken as the computational temperature value for target temperature control.

F4: Selecting all balloon circumference temperature values that are lower than the balloon center temperature value, and the lowest one of these balloon circumference temperature values lower than the balloon center temperature value is taken as the computational temperature value. If a number of the balloon circumference temperature values are lower than the balloon center temperature value, then the lowest one of the number of balloon circumference temperature values is taken as the computational temperature value for target temperature control.

Reference is now made to FIG. 5, which shows an image displayed on the display device during a practical ablation procedure. The balloon circumference temperature representation graphs include balloon circumference temperature condition graphs 11. Each balloon circumference temperature condition graph 11 may be displayed in a manner indicating a normal condition 111 or the first alert condition 112. The normal condition 111 indicates that the balloon circumference temperature value acquired from the corresponding circumference temperature sensor lies within the first threshold range, thus providing the operator with an indication that the temperature at the corresponding circumference portion of the cryoballoon 1 is appropriate. Preferably, the balloon circumference temperature condition graphs 11 are annularly arranged, to form an annulus as shown. Circumferential location of each of the balloon circumference temperature condition graphs 11 in the annulus is in correspondence with circumferential location of a corresponding circumference temperature sensor on the cryoballoon 1. Optionally, the balloon center temperature representation graph includes a numerical representation of the balloon center temperature value which is preferably displayed in a central area of the annulus.

In one exemplary embodiment, the balloon circumference temperature representation graphs include 8 balloon circumference temperature condition graphs 11 which are arc segments concentrically arranged into a ring, i.e., an annulus. Each arc segment represents a balloon circumference temperature value acquired from a circumference temperature sensor disposed on a circumference portion of the cryoballoon 1. Each balloon circumference temperature condition graph 11 may be displayed in different colors to indicate different temperature conditions of the respective circumference portions of the cryoballoon 1. For example, green (shown as blank in FIG. 5) indicates a normal condition 111, and red (shown as shaded in FIG. 5) indicates a first alert condition 112. In this way, the annulus can intuitively indicate whether the balloon circumference temperature values acquired from the circumference temperature sensors disposed on the respective circumference portions of the cryoballoon 1 are normal.

The first alert condition 112 includes a lower limit exceeded alert condition and an upper limit exceeded alert condition. The lower limit exceeded alert condition is a condition in which the balloon circumference temperature value acquired from the corresponding circumference temperature sensor is lower than a lower limit of the first threshold range. The upper limit exceeded alert condition is a condition in which the balloon circumference temperature value acquired from the corresponding circumference temperature sensor is higher than an upper limit of the first threshold range. For example, when the balloon circumference temperature value acquired from the circumference temperature sensor is lower than the lower limit of the first threshold range, the a lower limit exceeded alert condition may be displayed as flashing in red, indicating that the temperature of the balloon circumference portion corresponding to the circumference temperature sensor is excessively low and may cause serious damage and prompting the operator to adjust a temperature of a balloon. As another example, when the balloon circumference temperature value acquired from the circumference temperature sensor is higher than the upper limit of the first threshold range, the upper limit exceeded alert condition may be displayed continuously in red, indicating that the temperature of the balloon circumference portion corresponding to the circumference temperature sensor fails to drop into (remains higher than) the preset temperature range. This may be caused by inadequate occlusion of the balloon and may lead to a degraded ablation effect. Thus, the operator is prompted to confirm whether the balloon has achieved occlusion or adjust the location of the balloon. The first threshold range enabling effective ablation can be determined by comparison. Experiments have found that a balloon circumference portion with a favorable fit between its surface and an ablation site is expected to have a temperature lower than the balloon's center temperature, which enables the portion to provide a desirable cryoablation effect. On the contrary, a balloon circumference portion with an undesirable fit will have a temperature considerably higher than the balloon's center temperature, making it impossible to achieve effective ablation. It is to be noted that the first threshold range may alternatively be configured based on the operator's experience or on conventional configurations in the art. In addition, the normal condition 111 and the first alert condition 112 are not limited to being indicated by green and red. Rather, they may each be alternatively indicated by another color, sound, vibration, flashing or otherwise.

Preferably, the balloon circumference temperature representation graphs include a balloon circumference temperature curve plot 12. The balloon circumference temperature curve plot 12 includes curves of the balloon circumference temperature values acquired from the corresponding circumference temperature sensors varying over time. Referring to FIG. 7, the abscissa is time (in seconds(s)) and the ordinate is temperature (in degrees Celsius (° C.)). In one example, a balloon center temperature curve 120 extends around −35° C., and one balloon circumference temperature curve 121 extends substantially below −45° C., indicating a good fit between the surface of the balloon circumference portion corresponding to the curve 121 and the ablation site. However, there is another balloon circumference temperature curve 121' that extends above −10° C. This indicates a undesirable fit between the surface of the corresponding balloon circumference portion and the ablation site, which may lead to failure in achieving a good cryoablation effect and impaired clinical ablation effectiveness. Therefore, the balloon circumference temperature curve plot can provide the operator with an intuitive indication on ablation effect and is of great clinical value. The operator can choose to relocate the balloon and conduct target temperature (e.g., balloon center temperature) regulation. As a result of target temperature regulation, the balloon center temperature curve 120 in FIG. 7 may vary. In this way, the operator may know temperature evolution (i.e., temperature variation over time) by taking into account the variation of the curve 120. This can additionally provide intuitive reference and basis for temperature regulation.

Optionally, the balloon circumference temperature curve plot 12 may indicate the first alert condition. The indication of the first alert condition may include displaying the balloon circumference temperature curve in a flashing manner or in bold. Like the balloon circumference temperature condition graphs 11, the balloon circumference temperature curve plot 12 can also indicate the normal or first alert condition. When the balloon circumference temperature value acquired from one of the circumference temperature sensors lies within the first threshold range, the corresponding balloon circumference temperature curve 12 indicates the normal condition, for example, by displaying it as a normal curve. If the balloon circumference temperature value acquired from one of the circumference temperature sensors exceeds the first threshold range, then the corresponding balloon circumference temperature curve 12 indicates the first alert condition, for example, by displaying the curve as a flashing, bolded or otherwise colored curve. Of course, the first alert condition may be either the lower limit exceeded alert condition or the upper limit exceeded alert condition. Reference can be made to the above description in connection with the balloon circumference temperature condition graphs 11. In some other embodiments, the balloon circumference temperature representation graphs further include a lower limit temperature line 13 indicating the lower limit temperature of the first threshold range. This lower limit temperature line 13 is displayed together with the balloon circumference temperature curve plot 12 and as a straight line, as shown in FIG. 7, in order to facilitate the operator's perception of relationships between the temperature curves and the lower limit temperature line 13 and hence identification of whether there is an excessively low temperature. Of course, in some embodiments, the lower limit temperature line 13 may be used in combination with the balloon circumference temperature curve plot 12 indicating the first alert condition.

Preferably, the balloon circumference temperature representation graphs include a balloon graph 14. The balloon graph 14 includes dots 140 corresponding to the circumference temperature sensors and/or the center temperature sensor. The location of each dot 140 in the balloon graph 14 is in one-to-one correspondence with the location of a corresponding one of the circumference temperature sensors and/or the center temperature sensor on the cryoballoon 1. Preferably, each dot 140 corresponding to a corresponding one of the circumference temperature sensors corresponds to a corresponding one of the balloon circumference temperature curves 12 and a corresponding one of the balloon circumference temperature condition graphs 11. In practice, the balloon circumference temperature condition graphs 11 are essentially simple representations, which only indicate whether the temperatures of the balloon circumference portions are within the first threshold range to allow the operator immediately know temperature conditions of the individual balloon circumference portions. When the operator wants to access more detailed temperature information, he/she can navigate to such information (e.g., by pressing a button or by a touch). A displayed image containing the detail temperature information may provide the operator with the locations of the circumference temperature sensors on the balloon surface, the location of the center temperature sensor and real-time temperature information (e.g., in the form of the circumference temperature curves 12 shown in FIG. 7, or directly as numerical temperature values). Here, the dots 140 may be displayed to provide much information to the operator. Specifically, the dots 140 may have the same arrangement as that of the annulus. That is, the dots representing the circumference temperature sensors are arranged around the dot representing the center temperature sensor. Each dot 140 may indicate the same condition (normal or first alert) as the corresponding balloon circumference temperature condition graph 11. For example, when one of the balloon circumference temperature condition graphs 11 is displayed in green to indicate the normal condition, the corresponding dot 140 is also displayed in green to indicate the normal condition. When one of the balloon circumference temperature condition graphs 11 is displayed as flashing in red to indicate the first alert condition, the corresponding dot 140 does the same thing. For example, if a balloon circumference portion fails to fully fit a predetermined ablation site or is in pseudo-contact therewith, its temperature will decrease slowly, and the corresponding dot 140 in the balloon graph 14 will be displayed in a manner indicating the first alert condition. When the temperatures of some balloon circumference portions are not within the preset temperature range, the operator may perform one or more additional cryoablation processes and then check whether the temperatures of the balloon circumference portions have been tuned into the preset temperature range. If not, the operator may relocate the cryoballoon 1 by manipulating the catheter, and then perform another cryoablation process until complete ablation is achieved. If the temperatures of some balloon circumference portions are too low and considered to cause severe damage, the operator may interrupt the ongoing ablation process or to adjust a preset temperature and then check whether an abnormality has taken place.

In one preferred embodiment, the program in the readable storage medium may include the following interface modules:

a ready interface M1, an inflation interface M2, an ablation interface M3, a rewarming interface M4 and an ablation history interface, which will be described below in detail.

Referring to FIG. 2, the ready interface M1 includes historical ablation data of multiple ablation zones displayed on the display device 3 and press buttons allowing the operator to choose one of the ablation zones to be ablated by a press action. When the control device 2 is activated, a self-check is performed on a passage path of the catheter system and a connection between the cryoablation apparatus and the cryoballoon 1. During the self-check, the balloon center temperature value may be displayed in the ready interface M1 (e.g., "37° C.", as shown at the upper left corner of FIG. 2). In addition, historical pulmonary vein ablation data are also displayed in the ready interface M1, including ablation times and numbers of ablation processes. Generally, a cryoablation procedure requires ablation of all the four pulmonary veins, namely the left superior pulmonary vein (LSPV), the left inferior pulmonary vein (LIPV), the right superior pulmonary vein (RSPV) and the right inferior pulmonary vein (RIPV). Each pulmonary vein may be ablated one or more times. The historical ablation data displayed in the ready interface M1 are sorted by ablation site. The cryoablation history of each pulmonary vein is separately summarized and classified. Optionally, the ready interface M1 further includes the aforementioned balloon circumference temperature condition graphs 11.

Further, before each cryoablation process starts, the operator may select the pulmonary vein to be ablated by pressing a schematic icon thereof displayed in the ready interface M1. In response, information about the cryoablation process to be performed, including ablation time, temperature and other information, is recorded into a memory unit corresponding to the schematic icon of the selected pulmonary vein. At the same time, historical ablation information of the pulmonary vein may also be displayed in its schematic icon, for example, in the manner as described above in connection with FIG. 5. In the ready interface M1, a remaining amount of the gas may also be displayed (in the form of a percentage, e.g., "30%", as shown at the lower left corner of FIG. 2). The system may determine the remaining amount of the gas using any of many conventional techniques, such as weighing, gas pressure detection or the like. Therefore, this ready interface M1 is adapted mainly for initialization and the selection of a pulmonary vein to be ablated. Relevant data may be used for subsequent statistics. Optionally, the ready interface M1 may further include two press buttons, "Next" and "Complete". When "Next" is pressed, the inflation interface M2 is displayed. When "Complete" is pressed, the ablation procedure is completed.

Referring to FIG. 4, the inflation interface M2 displayed on the display device 3 includes inflation condition data of the balloon, including at least one of an internal pressure of the cryoballoon 1, the balloon center temperature value, an inflation time, an inflation flow rate and an inflation pressure. When "Next" in the ready interface M1 is pressed, the inflation interface M2 is displayed on the display device 3. At the same time, the cryoablation apparatus 2 starts inflating the cryoballoon 1 under the control of the control device 2, while the cryoballoon is cyroablated. The inflation interface M2 further includes a balloon inflation representation graph 15. Preferably, in the inflation interface M2, there are also displayed the balloon pressure (Pa) (i.e., the internal pressure of the cryoballoon 1), the inflation flow rate (e.g., "Flow Rate 0.41", as shown in a bottom portion of FIG. 4) and the inflation pressure (e.g., "Pressure 0.5", as also shown in the bottom portion of FIG. 4).

Optionally, the internal pressure of the cryoballoon 1 may be monitored by the cryoablation apparatus and displayed in the inflation interface M2 in real time. Accordingly, an internal pressure curve of the cryoballoon 1 is displayed in real time throughout the inflation process. The cryoballoon 1 is typically inflated for a fixed period of time. In the inflation process, a flow rate of the inflation gas is displayed. The internal pressure curve of the cryoballoon 1 over time is also displayed in real time, to allow a physician to easily determine whether the inflation process is safe or not, or whether it proceeds within a controlled range. The inflation process is carried out in an automated manner, and once it is completed, the system will be ready for ablation. Preferably, in the event of the internal pressure of the cryoballoon 1 exceeding a preset second threshold range, or of the balloon center temperature value exceeding a preset third threshold range, the inflation condition of the balloon will be displayed in a manner that indicates a second alert condition (e.g., by sound, flashing, a color change, a popup of a warning dialog box, or otherwise). Generally, during the inflation process, as cryoablation has not started yet, both the center and circumference temperatures of the cryoballoon 1 are typically 37° C. If there is a significant offset from this value, the system will provide an abnormality indication. On the basis of this, those skilled in the art may be set the third threshold range, e.g., as 37° C.±1° C. Likewise, if the internal process of the cryoballoon 1 is higher or lower than the second threshold range, the system will automatically raise an alarm and provide an error indication. Those skilled in the art can so set the second threshold range as to ensure that the internal pressure of the cryoballoon 1 stays within an appropriate range. Optionally, the inflation interface M2 may further include two press buttons, "Next" and "Previous". When "Next" is pressed, the ablation interface M3 will be displayed. When "Previous" is pressed, the ready interface M1 will be again displayed.

Referring to FIG. 5, the ablation interface M3 displayed on the display device 3 includes preset balloon temperature input field (e.g., "Temperature −55", as shown in the upper right corner of FIG. 5) and ablation time (e.g., "Time 180", as shown in the upper right corner of FIG. 5) input field, as well as press buttons, "Start", "Pause" and "Emergency Stop", which can be manipulated by the operator to make adjustments or operate the system. When the press button "Start" is pressed, the cryoballoon 1 performs a cryoablation process at the input preset balloon temperature and last for the input period of time. Based on a comparison between a comparative temperature value and the preset balloon temperature value, a flow rate adjustment is automatically made to the coolant. When the press button "Pause" is pressed, the ongoing cryoablation process is paused. When the press button "Emergency Stop" is pressed, the ongoing cryoablation process is ceased. A cryoablation process begins with the operator selecting a temperature to be preset (e.g., the balloon center temperature; of course, in some embodiment, the balloon circumference temperatures may be alternative preset). The operator may preset a temperature value through the preset balloon temperature input field. Moreover, a duration of the ablation time may also be set through the ablation time input field. Once a temperature value is preset, the cryoablation apparatus will enter a temperature control mode, in which, during cryoablation, the lowest balloon center temperature value is controlled to be not lower than the preset value. This temperature control function can be performed, for example, by a control algorithm in the cryoablation apparatus. Preferably, the ablation interface M3 further includes the above-described balloon circumference representation graph and center temperature representation graph. The balloon circumference temperature representation graphs may, for example, include a plurality of balloon circumference temperature condition graphs 11 arranged into an annulus and a circumference temperature curve plot. During the surgical procedure, based on the balloon circumference and center temperature representation graphs displayed in the ablation interface M3, once an excessively high or low temperature is identified, the operator can adjust the preset temperature in a timely way through manipulating the ablation interface M3. Thus, the balloon circumference and center temperature representation graphs can provide real-time support to the operator's decision-making about cryoablation temperature. Optionally, in order to provide more support to the operator, real-time data may be further displayed in the ablation interface M3, including a remaining amount of the gas (in the form of a percentage, e.g., "30%", as shown at the lower left corner of FIG. 2), a real-time inflation flow rate (e.g., "Flow Rate 0.41", as shown at the lower left corner of FIG. 5) and an inflation pressure (e.g., "Pressure 0.5", as shown in a bottom portion of FIG. 5).

Preferably, when the press button "Start" in the ablation interface M3 is pressed, the system derives a computational temperature value from the balloon circumference temperature values by using a predefined algorithm, and based on a comparison between the computational temperature value and the preset balloon temperature value, a flow rate adjustment is made to the coolant, thus accomplishing a temperature adjustment to the cryoballoon 1. In general, cryoablation temperature control is accomplished by adjusting the flow rate of the coolant. Throughout the cryoablation process, PID control is applied during flow rate rising and plateau phases. During the flow rate rising phase, proportional control is applied to prevent a flow rate overshoot. For example, for the control temperature being set to −45° C., the corresponding proportional control may be implemented to achieve 350 psi, 400 psi, 440 psi, 470 psi, 490 psi. This proportional control in the early phase allows the flow rate to rise as fast as possible while being adapted to various temperature options to prevent flow rate and temperature overshooting during the control process. Pressures in the proportional control may be achieved using a solenoid valve or a proportional valve. The control cycle may be determined depending on the actual circumstances, e.g., as 0.5 s. The temperature may be controlled to fluctuate within a certain range around the target temperature, e.g., ±3° C. Of course, those skilled in the art may appropriately configure the cryoablation temperature control as actually required.

Optionally, a number of preset balloon temperature options may be provided, and the operator may choose one from them. Of course, in some embodiments, no such options may be provided. In such embodiments, a cryoablation mode without temperature control will be activated. Preferably, after the preset balloon temperature and ablation time have been preset, the operator may press the press button "Start". In the course of ablation, a period of time the current ablation process has lasted for and a total ablation time will be displayed. Preferably, a balloon inflation representation graph 15 is also displayed in the ablation interface M3.

Preferably, the operator may determine whether effective ablation has been achieved based on his/her own experience. For example, when an effective temperature has been reached and maintained for a certain period of time, the operator may determine that effective ablation has been achieved. In addition, the ablation time, cryoablation temperature and the like may be preset at his/her own discretion. If an abnormality occurs and is displayed by the ablation interface M3, the operator may stop the ablation process by pressing the button "Emergency Stop" or "Pause".

When cryoablation is completed at one ablation site, a rewarming process is initiated. The rewarming process is essentially shown in the rewarming interface M4 displayed on the display device 3. Referring to FIG. 8, when the supply of the cryogenic gas to the cryoballoon catheter is cut off, a plurality of balloon circumference temperature representation graphs (e.g., the aforementioned balloon circumference temperature representation graphs 11 that are arranged into an annulus), a balloon center temperature representation graph, a rewarming time (e.g., "Time (s) 120", as shown in an top portion of FIG. 8) and the internal pressure of the cryoballoon catheter (e.g., the balloon pressure (Pa) curve in FIG. 8) are displayed in the rewarming interface M4 on the display device 3. The rewarming process is a process following the cessation of the cryogenic gas supply to the balloon, in which the balloon remaining inflated is gradually heated up by blood from the low temperature to the cardiac temperature. This process is passive, and generally, the only thing the operator is required to do is to observe it. From the balloon circumference temperature representation graphs, the balloon center temperature representation graph and the internal pressure curve of the cryoballoon 1 that are displayed in the rewarming interface M4, the operator can know balloon conditions during the rewarming process and the progress of the process. As known from the best practice of cryoablation, a slower rewarming speed indicates a better fit of the balloon and hence a better therapeutic treatment effect that can be obtained. Therefore, the intuitive display of the balloon circumference temperature representation graphs is of certain value in helping the operator predict the therapeutic treatment effect. Optionally, in order to provide more support to the operator, real-time data may be further displayed in the rewarming interface M4, including a remaining amount of the gas (in the form of a percentage, e.g., "30%", as shown at the lower left corner of FIG. 2), a real-time inflation flow rate (e.g., "Flow Rate 0.41", as shown in a bottom portion of FIG. 8), an inflation pressure (e.g., "Pressure 0.5", as shown in a bottom portion of FIG. 8), a balloon inflation representation graph 15 and a total time of the current ablation process (e.g., "Total Time (s) 400", as shown at the upper right corner of FIG. 8).

Preferably, the rewarming interface M4 further includes press buttons, "Vacuumize" and "Complete". When "Vacuumize" is pressed, the cryoballoon 1 is evacuated and brought into a collapsed configuration that facilitates its withdrawal or relocation. When "Complete" is pressed, the system switches back to the ready interface M1. The cryoablation process ends upon the completion of rewarming and vacuumization. When the cryoballoon 1 needs to perform another ablation process at the same site or at another pulmonary vein site, the operator can press the button "Complete" to get the system ready for the next ablation process. Thus, the ablation process can be repeated at the operator's discretion based on his/her experience until the whole cryoablation procedure is completed.

In summary, in the catheter system of the present invention, based on balloon circumference temperature values obtained by a plurality of circumference temperature sensors circumferentially disposed on a cryoballoon catheter, a plurality of balloon circumference temperature representation graphs are displayed on a display device. Moreover, based on a balloon center temperature value obtained by a center temperature sensor disposed at a center of the cryoballoon catheter, a balloon center temperature representation graph is displayed on the display device. The balloon circumference temperature representation graphs are displayed in such an intuitive manner that they surround the balloon center temperature representation graph. In the event of any one of the balloon circumference temperature values exceeding a predetermined first threshold range, a corresponding one of the balloon circumference temperature representation graphs is displayed in a manner indicating a first alert condition, promoting an operator to adjust temperature of the cryoballoon. A preset balloon temperature is received in an input field displayed on the display device, and based on a comparison between the preset balloon temperature value and a comparative temperature value, a flow rate adjustment is automatically made to a coolant introduced into the cryoballoon, thus achieving temperature control of the cryoballoon. The comparative temperature value is the balloon center temperature value, any one of the balloon circumference temperature values, or a computational temperature value derived by a predefined algorithm from the plurality of balloon circumference temperature values. With this arrangement, on the one hand, it is allowed to determine whether the temperatures of the individual cryoballoon portions stay within the appropriate temperature range in an intuitive manner. Moreover, in the event of the temperature of any cryoballoon portion exceeding the predetermined first threshold range, the corresponding balloon circumference temperature representation graph is displayed in a manner indicating the first alert condition, thereby guiding the operator to adjust temperature of the cryoballoon. On the other hand, the input field provided on the display device can receive the preset balloon temperature from the operator, and the system then compares the preset balloon temperature value with the comparative temperature value. Based on the comparison, a flow rate adjustment is automatically made to the coolant, thereby achieving temperature control of the cryoballoon in a simple and reliable manner. In particular, since the comparative temperature value may be the balloon center temperature value, or any one of the balloon circumference temperature values, or a computational temperature value derived by the predefined algorithm from the plurality of balloon circumference temperature values, the system is widely applicable and highly accurate.

The description presented above is merely that of some preferred embodiments of the present invention and is not intended to limit the scope thereof in any sense. Any and all changes and modifications made by those of ordinary skill in the art based on the above teachings fall within the scope as defined in the appended claims.

What is claimed is:

1. A cryoballoon catheter system, comprising a control device, a cryoballoon catheter and a display device, wherein the cryoballoon catheter comprises a cryoballoon, a center temperature sensor disposed at a center of the cryoballoon and a plurality of circumference temperature sensors circumferentially disposed on the cryoballoon, wherein each of the center temperature sensor and the circumference temperature sensors is communicatively connected to the control device, wherein the display device is communicatively connected to the control device, wherein the display device is provided with an input field for receiving a preset balloon temperature;

wherein the control device is connected to the cryoballoon catheter and is configured to:

acquire a plurality of balloon circumference temperature values obtained by a plurality of circumference temperature sensors of the cryoballoon catheter, and a balloon center temperature value obtained by a center temperature sensor of the cryoballoon catheter; and automatically adjust a flow rate of coolant introduced into a cryoballoon in the cryoballoon catheter based on a comparison between a preset balloon temperature value and a comparative temperature value to enable a temperature control of the cryoballoon, wherein the comparative temperature value is the balloon center temperature value, or any one of the plurality of balloon circumference temperature values, or a computational temperature value derived by a predefined algorithm from the plurality of balloon circumference temperature values, wherein the cryoballoon catheter system is configured to:

display a balloon center temperature representation graph on the display device based on the balloon center temperature value; and display a plurality of balloon circumference temperature representation graphs on the display device based on the plurality of balloon circumference temperature values, wherein the plurality of balloon circumference temperature representation graphs surround the balloon center temperature representation graph;

wherein each balloon circumference temperature representation graph comprises a balloon circumference temperature condition graph configured to indicate a normal condition or a first alert condition, wherein the normal condition indicates that the balloon circumference temperature value obtained by the corresponding circumference temperature sensor lies within the first predetermined threshold range, so prompts the operator that a temperature of the cryoballoon is appropriate, and in an event of any one of the plurality of balloon circumference temperature values exceeding a first predetermined threshold range, a corresponding one of the balloon circumference temperature representation graphs indicates the first alert condition to prompt an operator to adjust a temperature of the cryoballoon.

2. The cryoballoon catheter system according to claim 1, wherein a plurality of the balloon circumference temperature condition graphs are annularly arranged to form an annulus, wherein a circumferential location of each of the balloon circumference temperature condition graphs in the annulus is in correspondence with a circumferential location of a corresponding circumference temperature sensor on the cryoballoon.

3. The cryoballoon catheter system according to claim 1, wherein the first alert condition comprises a lower limit exceeded alert condition and an upper limit exceeded alert condition, wherein the lower limit exceeded alert condition indicates that the balloon circumference temperature value obtained by the corresponding circumference temperature sensor is lower than a lower limit of the first threshold range, and wherein the upper limit exceeded alert condition indicates that the balloon circumference temperature value obtained by the corresponding circumference temperature sensor is higher than an upper limit of the first threshold range.

4. The cryoballoon catheter system according to claim 1, wherein the cryoballoon catheter system is configured to display a balloon circumference temperature representation graph on the display device based on the plurality of balloon circumference temperature values, and wherein the balloon circumference temperature representation graph comprises a balloon circumference temperature curve plot, wherein the balloon circumference temperature curve plot comprises curves of the balloon circumference temperature values obtained by the corresponding circumference temperature sensors varying over time.

5. The cryoballoon catheter system according to claim 4, wherein the balloon circumference temperature curve plot comprises an indication of the first alert condition, wherein the first alert condition comprises a flashing or bold display of the balloon circumference temperature curve plot, and/or wherein the balloon circumference temperature representation graph further comprises a lower limit temperature line of the first threshold range.

6. The cryoballoon catheter system according to claim 1, wherein the cryoballoon catheter system is configured to display a balloon circumference temperature representation graph on the display device based on the plurality of balloon circumference temperature values and/or the balloon center temperature value, the balloon circumference temperature representation graph comprises a balloon graph, wherein the balloon graph comprises a plurality of dots corresponding to the plurality of circumference temperature sensors and/or a dot corresponding to the center temperature sensor, wherein a location of each dot in the balloon graph is in correspondence with a location of a corresponding one of the circumference temperature sensors and/or the center temperature sensor on the cryoballoon.

7. The cryoballoon catheter system according to claim 1, further configured to: display historical ablation data of a plurality of ablation zones on the display device and provide press buttons for the operator to select one of current ablation zones.

8. The cryoballoon catheter system according to claim 1, further configured to display inflation condition of the cryoballoon on the display device, wherein the inflation condition of the cryoballoon comprise at least one of: an internal pressure of the cryoballoon, the balloon center temperature value, an inflation time, an inflation flow rate and an inflation pressure.

9. The cryoballoon catheter system according to claim 8, wherein in an event of the internal pressure of the cryoballoon exceeding a second predetermined threshold range, or of the balloon center temperature value exceeding a third predetermined threshold range, the inflation condition of the cryoballoon is displayed in a manner indicating a second alert condition.

10. The cryoballoon catheter system according to claim 1, further configured to:

provide, on the display device, an input field for receiving an ablation time and press buttons, "Start", "Pause" and "Emergency Stop", wherein when the press button "Start" is pressed, the cryoballoon catheter performs a cryoablation operation according to the received preset balloon temperature and an ablation time, and the system automatically adjusts a flow rate to the coolant based on a comparison between the comparative temperature value and the preset balloon temperature value, wherein when the press button "Pause" is pressed, the system pauses the cryoablation operation, and wherein when the press button "Emergency Stop" is pressed, the system stops performing the cryoablation operation.

11. The cryoballoon catheter system according to claim 10, wherein when the press button "Start" is pressed, the display device is further configured to display at least one of: a curve of the computational temperature value varying over time, an internal pressure of the cryoballoon and the ablation time.

12. The cryoballoon catheter system according to claim 1, further configured to:

after a cryogenic gas supply to the cryoballoon catheter is cut off, display, on the display device, the plurality of balloon circumference temperature representation graphs, a balloon center temperature representation graph, a rewarming time and an internal pressure of the cryoballoon.

13. A temperature display method using the cryoballoon catheter system according to claim 1.

14. The temperature display method according to claim 13 wherein a plurality of the balloon circumference temperature condition graphs are annularly arranged to form an annulus, and wherein a circumferential location of each of the balloon circumference temperature condition graphs in the annulus is in correspondence with a circumferential location of the corresponding circumference temperature sensor on the cryoballoon.

15. The temperature display method according to claim 13, wherein the cryoballoon catheter system is configured to display a balloon circumference temperature representation graph on the display device based on the plurality of balloon circumference temperature values and/or the balloon center temperature value, wherein the balloon circumference temperature representation graph comprises a balloon graph, wherein the balloon graph comprises a plurality of dots corresponding to the plurality of circumference temperature sensors and/or a dot corresponding to the center temperature sensor, wherein a location of each dot in the balloon graph is in correspondence with a location of a corresponding one of the circumference temperature sensors and/or the center temperature sensor on the cryoballoon.

16. The temperature display method according to claim 13, wherein the cryoballoon catheter system is configured to display a balloon circumference temperature representation graph on the display device based on the plurality of balloon circumference temperature values, wherein the balloon circumference temperature representation graph comprises a balloon circumference temperature curve plot, wherein the balloon circumference temperature curve plot comprises curves of the balloon circumference temperature values obtained by the corresponding circumference temperature sensors varying over time.

17. The cryoballoon catheter system according to claim 1, wherein when the comparative temperature value is a computational temperature value derived by a predefined algorithm from the plurality of balloon circumference temperature values, the predefined algorithm comprises any one of:

determining a lowest one of the plurality of balloon circumference temperature values as the computational temperature value;

determining an average of the plurality of balloon circumference temperature values as the computational temperature value;

determining an average of the balloon circumference temperature values that are lower than the balloon center temperature value as the computational temperature value; and determining a lowest one of the balloon circumference temperature values that are lower than the balloon center temperature value as the computational temperature value.

* * * * *